(12) United States Patent
Brabec et al.

(10) Patent No.: US 7,945,337 B2
(45) Date of Patent: May 17, 2011

(54) HIGH IMPEDANCE AND LOW POLARIZATION ELECTRODE

(75) Inventors: Scott J. Brabec, Elk River, MN (US); Jordon D. Honeck, Maple Grove, MN (US); William J. Schindeldecker, Foreston, MN (US)

(73) Assignee: Medtronic, Inc., Minneapolis, MN (US)

( * ) Notice: Subject to any disclaimer, the term of this patent is extended or adjusted under 35 U.S.C. 154(b) by 298 days.

(21) Appl. No.: 10/648,908

(22) Filed: Aug. 27, 2003

(65) Prior Publication Data
US 2005/0049665 A1 Mar. 3, 2005

(51) Int. Cl.
*A61N 1/05* (2006.01)
(52) U.S. Cl. .................. 607/122; 607/120; 607/127
(58) Field of Classification Search .............. 607/122, 607/121, 127, 131, 120, 104
See application file for complete search history.

(56) References Cited

U.S. PATENT DOCUMENTS

| | | | | |
|---|---|---|---|---|
| 3,476,116 A | 11/1969 | Parsonnet et al. | ............. | 128/417 |
| 3,749,101 A | 7/1973 | Williamson | ................. | 128/418 |
| 3,981,309 A | 9/1976 | Cannon | ...................... | 128/419 P |
| 4,313,443 A | 2/1982 | Lund et al. | ................... | 128/642 |
| 4,440,178 A | 4/1984 | Bussard et al. | .............. | 128/784 |
| 4,502,492 A | 3/1985 | Bornzin | ........................ | 128/785 |
| 4,953,564 A * | 9/1990 | Berthelsen | .................... | 607/120 |
| 5,282,844 A * | 2/1994 | Stokes et al. | ................. | 607/120 |
| 5,324,325 A * | 6/1994 | Moaddeb | ...................... | 607/120 |
| 5,408,744 A * | 4/1995 | Gates | ............................ | 29/875 |
| 5,431,649 A * | 7/1995 | Mulier et al. | ................ | 607/120 |
| 5,443,492 A | 8/1995 | Stokes et al. | .................. | 607/131 |
| 5,456,708 A | 10/1995 | Doan et al. | ..................... | 607/127 |
| 5,458,630 A | 10/1995 | Hoegnelid et al. | ........... | 607/116 |
| 5,871,526 A | 2/1999 | Gibbs et al. | .................... | 607/104 |
| 5,871,529 A | 2/1999 | Bartig et al. | ................... | 607/122 |
| 5,906,613 A * | 5/1999 | Mulier et al. | ................... | 606/41 |
| 5,948,015 A | 9/1999 | Hess et al. | ..................... | 607/127 |

(Continued)

FOREIGN PATENT DOCUMENTS

| EP | 0 057 877 | 8/2002 |
|---|---|---|
| WO | WO 00/25854 | 5/2000 |

OTHER PUBLICATIONS

"Ringer's solution." The American Heritage Stedman's Medical Dictionary. Houghton Mifflin Company, 2002. Answers.com GuruNet Corp. Aug. 4, 2005. http://www.answers.com/topic/ringer-s-solution.*

Bolz, A. et al., "Tin Coated Pacemaker Leads for Reliable Capture Recognition in Human Heart," *International Journal of Artificial Organs*, vol. 15, No. 9, p. 561 (1992).

(Continued)

*Primary Examiner* — Niketa I Patel
*Assistant Examiner* — Alyssa M Alter
(74) *Attorney, Agent, or Firm* — Carol F. Barry

(57) ABSTRACT

An insulative housing formed about a distal end of a medical electrical lead body includes a cavity and a port; an ionically conductive medium fills the cavity and is in intimate contact with an electrode surface contained within the cavity. When a current is delivered to the electrode surface contained within the cavity, a first current density generated at the electrode surface is smaller than a second current density generated out from the port of the insulative housing; thus, the port forms a high impedance and low polarization tissue-stimulating electrode.

17 Claims, 3 Drawing Sheets

U.S. PATENT DOCUMENTS

| | | | |
|---|---|---|---|
| 6,086,582 A * | 7/2000 | Altman et al. | 606/41 |
| 6,097,986 A | 8/2000 | Janke et al. | 607/127 |
| 6,129,751 A * | 10/2000 | Lucchesi et al. | 607/127 |
| 6,298,272 B1 * | 10/2001 | Peterfeso et al. | 607/120 |
| 6,360,129 B1 * | 3/2002 | Ley et al. | 607/120 |
| 6,430,447 B1 | 8/2002 | Chitre et al. | 607/121 |
| 6,501,994 B1 | 12/2002 | Janke et al. | 607/127 |

OTHER PUBLICATIONS

Mauro, "Capacity Electrode for Chronic Stimulation," *Science*, vol. 132, p. 356 (1960).

* cited by examiner

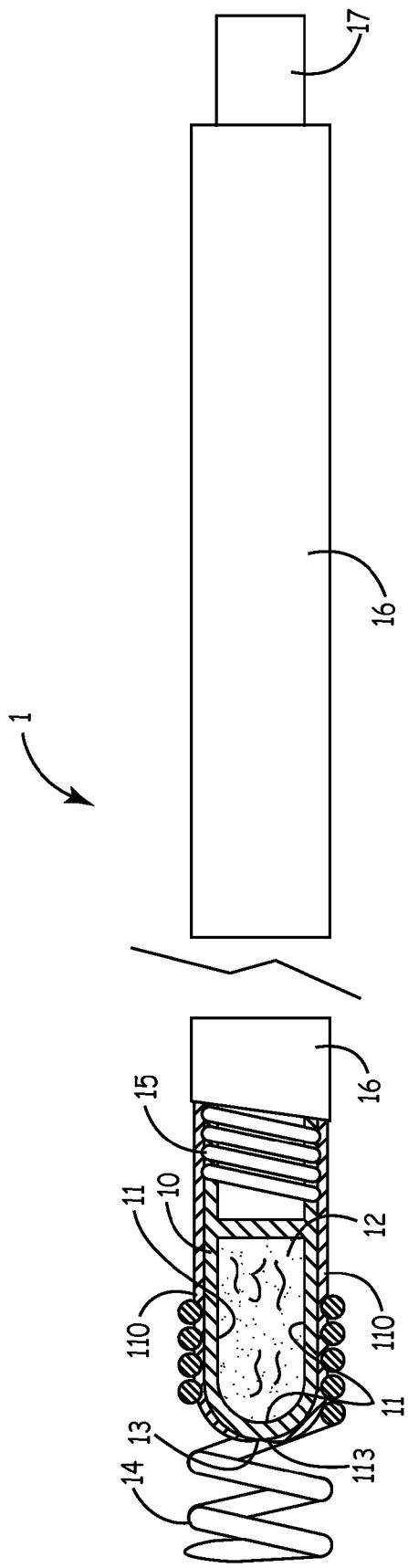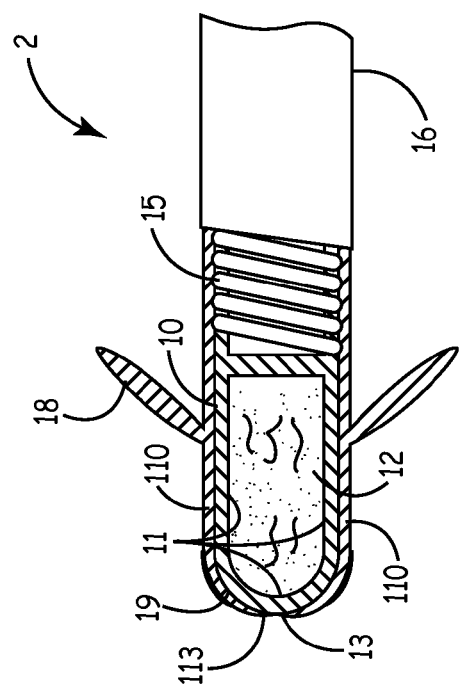

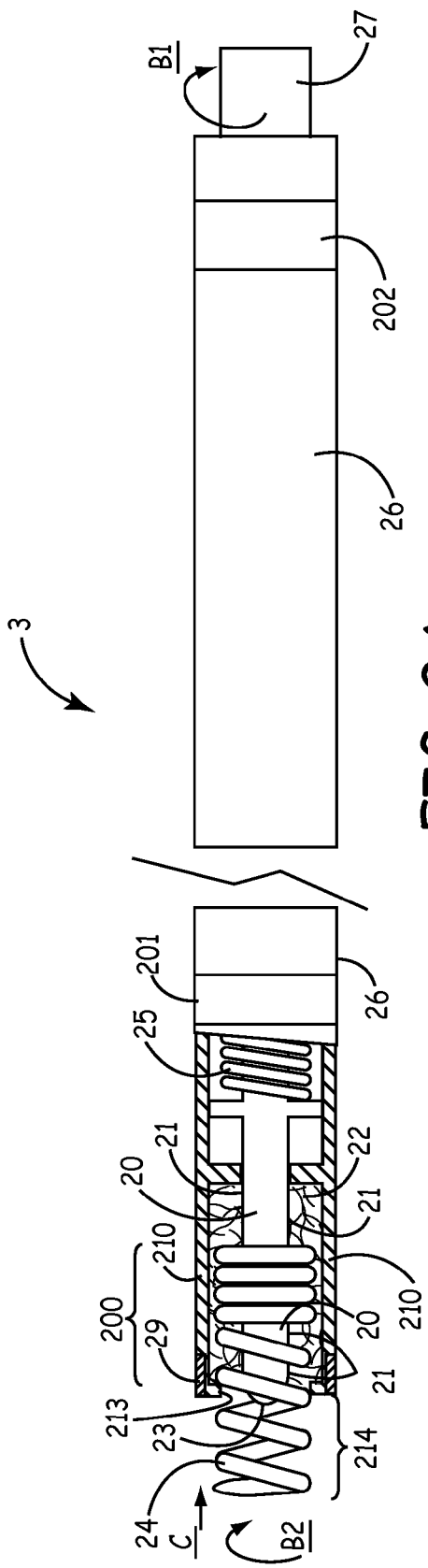
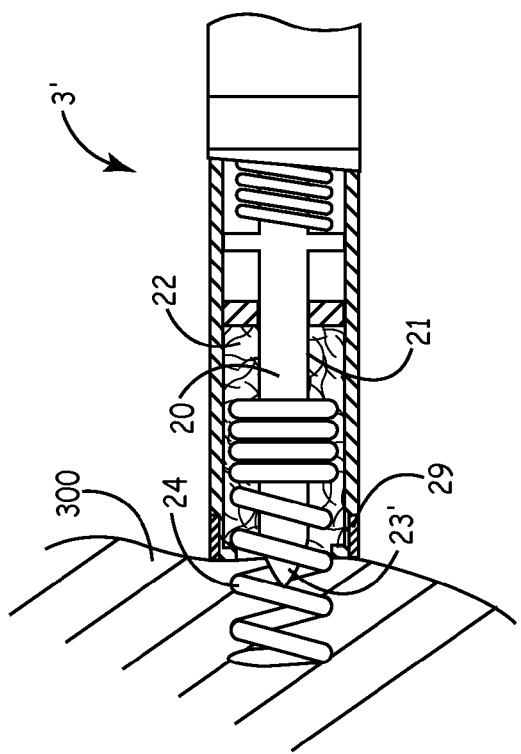
FIG. 2A
FIG. 2B

HIGH IMPEDANCE AND LOW POLARIZATION ELECTRODE

TECHNICAL FIELD

The present invention relates to medical electrical leads and more particularly to high impedance and low polarization electrodes.

BACKGROUND

Implantable medical devices have long utilized medical electrical leads, which include an electrode adapted for pacing myocardial tissue via intimate tissue contact with a surface of the electrode. An alternative pacing electrode, generally described by Parsonnet et al. as a differential current density (DCD) electrode in "Clinical use of a new transvenous electrode" Annals New York Academy of Science, Oct. 30, 1969, 167:756-760, includes an electrode surface, in the form of a cylinder, contained within an insulative housing and thus separated from tissue contact. The DCD electrode described by Parsonnet et al. makes stimulating contact with endocardial tissue via a hole or port in the insulative housing; when a current is applied the density of the current at the electrode surface is low relative to that at the hole, thus the differential current density. A higher current density at the interface between the hole and endocardial tissue results in lower stimulation thresholds, while a lower current density along the electrode surface within the insulative housing minimizes polarization; polarization, resulting from an accumulation of charge on an electrode surface post-stimulation, produces an after-potential that hinders accurate sensing of intrinsic cardiac activity. Such an electrode necessarily includes an ionically conductive medium filling a void between the electrode surface contained within the insulative housing and the hole in contact with the myocardium. A stable conductive medium incorporated into a DCD-type electrode along with means to maintain stable long-term contact between a hole or a port of such an electrode and excitable tissue are desirable.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and:

FIG. 1A is a plan view including a partial section of a medical electrical lead including a DCD electrode according to one embodiment of the present invention;

FIG. 1B is a plan view including a partial section of a distal portion of a medical electrical lead including a DCD electrode according to another embodiment of the present invention;

FIG. 2A is a plan view including a partial section of a medical electrical lead including a DCD electrode according to an alternate embodiment of the present invention;

FIG. 2B is a plan view including a partial section of a distal portion of a medical electrical lead including a DCD electrode, according to yet another embodiment, fixed within a segment of tissue;

DETAILED DESCRIPTION

Figure 3A:
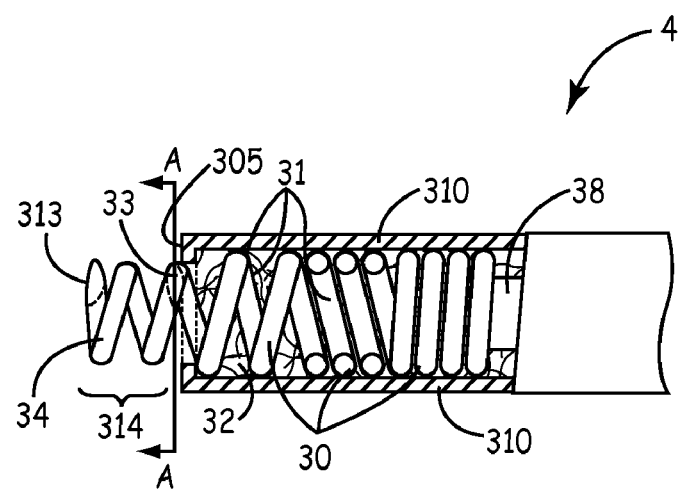
FIG. 3A is a plan view including a partial section of a distal portion of a medical electrical lead including a DCD electrode according to additional embodiments of the present invention.

The following description is exemplary in nature and is not intended to limit the scope, applicability, or configuration of the invention in any way. Rather, the following description provides a practical illustration for implementing exemplary embodiments of the invention.

FIG. 1A is a plan view including a partial section of a medical electrical lead including a DCD electrode according to one embodiment of the present invention. FIG. 1A illustrates a lead 1 including an elongated body formed by a insulative sheath 16 and a conductor 15 extending therein; conductor 15 couples a connector pin 17 terminating a proximal end of the body to a conductive structure 10 contained within an insulative housing 110 formed about a distal end of the body of a material such as polyurethane or silicone. Conductor 15 delivers current to conductive structure 10 from connector pin 17 and may be joined to connector pin 17 and to conductive structure 10 by welding, crimping, or by other means known to those skilled in the art of lead construction; furthermore conductor 15 and sheath 16 may be formed of materials well known to those skilled in the art, for example MP25N alloy and silicone or polyurethane, respectively. The proximal end of the body including connector pin 17 may conform to an industry standard for mating with a connector port of an implantable medical device.

FIG. 1A further illustrates conductive structure 10 including a first electrode surface 11, a second electrode surface 13 and a cavity 12. An insulated helical fixation member 14 is coupled to insulative housing 110 and extends distally in order to affix second electrode surface 13 against a segment of tissue via rotation of fixation member 14 as is well known to those skilled in the art. Fixation member 14 may be formed of a non-conductive biocompatible material, for example a rigid polymer such as PEEK, or a ceramic, or of a conductive material including a biocompatible insulative coating, for example stainless steel having a parylene coating or tantalum having an oxide coating.

According to embodiments of the present invention cavity 12 enclosed by first electrode surface 11 is filled with an ionically conductive medium in intimate contact with first electrode surface 11; first surface 11 has a surface area approximately greater than or equal to approximately 10 square millimeters, and port 113 circumscribes second electrode surface 13, which has a surface area between approximately 0.1 square millimeters and 4 square millimeters, to form a high impedance and low polarization DCD electrode wherein a relatively high current density is formed at second electrode surface 13 and a relatively low current density is formed at first electrode surface 11 when a current is delivered from connector pin 17 to conductive structure 10 via conductor 15. The ionically conductive medium may be introduced into cavity 12 via an opening (not shown) in conductive structure 10 either prior to or after assembly of conductive structure 10 into insulative housing 110; the opening may be sealed by welding a cap thereover or bonding a plug therein. Conductive structure 10 is made of a platinum-iridium alloy according to one embodiment of the invention and the conductive medium filling cavity 12 comprises a hydrated hydrogel, examples of which include but are not limited to a polyacrylamide, according to one embodiment, and a saline solution according to another embodiment. Although FIG. 1A illustrates second electrode surface 13 approximately flush with port 113 according to an alternate embodiment second electrode surface 13 may protrude from port 113. The relatively high current density formed at second electrode surface 13 allows for lower tissue-stimulation voltages resulting from high impedance due to the smaller surface area contacting tissue, while the relatively low current density formed at first electrode surface 11 interfacing with the conductive medium filling cavity 12 results from the larger surface area and eliminates significant polarization that may hinder post-stimulation sensing.

According to one embodiment of the present invention, since first electrode surface 11 has a relatively large surface area to reduce polarization, second electrode surface 13 need not have a large microscopic surface area as is typical of some state of the art high impedance electrode surfaces, therefore second electrode surface 13 may be smooth such that a microscopic surface area of second electrode surface 13 is not significantly greater than a macroscopic surface area of second electrode surface 13. According to additional alternate embodiments, first electrode surface 11 is microscopically enlarged by means of surface modifications known to those skilled in the art of electrode design, examples of which include but are not limited to iridium-oxide and ruthenium-oxide deposited electrochemically, by thermal deposition or by sputtering, electrochemically deposited platinum black particles, and sputtered titanium-nitride. Further embodiments include those in which second electrode surface 13 is likewise microscopically modified.

FIG. 1B is a plan view including a partial section of a distal portion of a medical electrical lead including a DCD electrode according to another embodiment of the present invention. FIG. 1B illustrates lead 2 including many elements in common with lead 1 illustrated in FIG. 1A but a set of resilient tine members 18 replaces insulated helical fixation element 14 to assist in holding second electrode surface 13 circumscribed by port 113 in contact with tissue according to means known to those skilled in the art. FIG. 1B further illustrates lead 2 including a steroid-loaded monolithic controlled release device (MCRD) 19 formed about insulative housing 110 in proximity to port 113. Steroid-loaded MCRD 19 reduces inflammation of contacting tissue and, according to one embodiment, is a biocompatible polymer matrix impregnated with dexamethasone phosphate, either adhered to an integral part of insulative housing 110; additional materials comprising steroid-loaded MCRD's and methods for forming them are well known to those skilled in the art.

FIG. 2A is a plan view including a partial section of a medical electrical lead including a DCD electrode according to an alternate embodiment of the present invention. FIG. 2A illustrates a lead 3 including an elongated body formed by a insulative sheath 26 and a first insulated conductor 25 and a second conductor (not shown) extending therein; first insulated conductor 25 couples a connector pin 27 terminating a proximal end of the body to a conductive structure 20 contained within an insulative housing 210 formed about a distal end of the body and second conductor couples a connector ring 202, positioned in proximity to connector pin 27, to an electrode ring 201. First insulated conductor 25 may be joined to connector pin 17 and to conductive structure 20 by welding, crimping, or by other means known to those skilled in the art of lead construction; furthermore first insulated conductor 25 and sheath 26 may be formed of materials well know to those skilled in the art, for example MP35N alloy covered by an insulative polymer, for example ETFE or polyimide, and silicone or polyurethane, respectively. The second conductor may be joined to connector ring 202 and electrode ring 201 in a similar manner and be likewise formed of an MP35N alloy. The proximal end of the body including connector pin 27 and connector ring 202 may conform to an industry standard for mating with a connector port of an implantable medical device.

FIG. 2A further illustrates conductive structure 20 contained within a cavity 22 of insulative housing 210 and formed as a stud joining conductor 25 to an insulated helical fixation element 24 which extends distally out from a port 213 of insulative housing 210; conductive structure 20 includes a first electrode surface 21 in intimate contact with an ionically conductive medium filling cavity 22 and a second electrode surface 23 protruding from port 213, which is brought into contact with tissue by means of insulated helical fixation member 24. The conductive medium filling cavity 22 may comprise a hydrogel or a saline solution, as previously described, or blood, which enters cavity 22 through port 213 as lead 3 is being implanted. FIG. 2A also depicts a steroid-loaded MCRD 29 formed in proximity to port 213 similar to that described in conjunction with FIG. 1B. According to embodiments of the present invention surface areas of first electrode surface 21 and second electrode surface 23 are the same as those previously described in conjunction with FIG. 1A in order to create high impedance at second surface 23 and low polarization with first surface 21; furthermore, first surface 21 may include a large microscopic surface area via coatings as previously described and second surface 23 may be smooth as previously described.

According to some embodiments of the present invention fixation member 24 is formed of a conductive material having an insulative coating, as previously described, and includes a proximal extension 200 contained within cavity 22, which is free of the coating in order to augment first electrode surface 21. According to additional embodiments, a distal portion 214 of fixation member 24 is retractable into insulative housing 210 by means of rotating connector pin 27 per arrow B1 which causes fixation member 24 to rotate per arrow B2 and translate into housing 210 per arrow C, via torque transfer through conductor 25 and stud 20; fixation member 24 is also extendable from housing 210 via rotation of connector pin 27 in a direction opposite arrow B1; such mechanisms are well known to those skilled in the art.

FIG. 2B is a plan view including a partial section of a distal portion of a medical electrical lead including a DCD electrode, according to yet another embodiment, fixed within a segment of tissue 300. FIG. 2B illustrates a lead 3' wherein conductive structure or stud 20 includes a second electrode surface 23' formed to pierce tissue 300 when fixation member 24 is screwed into tissue 300. Second surface 23' is smooth as previously described or microscopically modified as previously described.

Figure 3B:
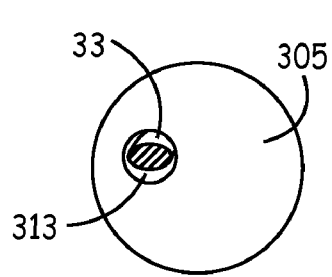
FIGS. 3B-C are end views through section line A-A of FIG. 3A showing alternate embodiments of a DCD electrode.
Figure 3C:
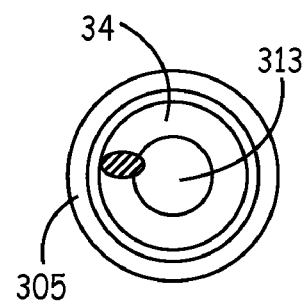

FIG. 3A is a plan view including a partial section of a distal portion of a medical electrical lead including a DCD electrode according to additional embodiments of the present invention and FIGS. 3B-C are end views through section line A-A of FIG. 3A showing alternate embodiments of the DCD electrode. FIG. 3A illustrates a distal portion of a lead 4, which may terminate either of the lead bodies previously described in conjunction with FIGS. 1A and 2A; lead 4 includes a conductive structure 30, formed by a proximal extension of helical fixation member 34, having a first electrode surface 31 in intimate contact with an ionically conductive medium filling cavity 32 of an insulative housing 310.

Fixation member 34 is joined to a stud 38, which in turn is joined to an elongated conductor (not shown) and the conductor delivers a current to conductive structure 30, in a manner similar to that previously described.

FIGS. 3A-B illustrate a second electrode surface 33 of conductive structure 30 formed as a segment of fixation member 34 positioned in proximity to a port 313 of insulative housing 310, extending from a distal end 305, and proximally adjacent to an insulated portion 314 of fixation member 34; according to this embodiment, a surface area of second electrode surface 33 is small enough to create a high impedance while a surface area of first electrode surface 31 is large enough to prevent significant polarization. It should be noted that, according to an alternate embodiment, first electrode surface 31 is positioned at a distal tip 313 of fixation member 34 by removing an insulative coating in this zone.

FIG. 3C illustrates an alternate embodiment wherein insulated portion 314 of fixation member 34 does not include a zone free of insulation forming a second electrode surface as described in conjunction with FIG. 3B; rather, the conductive medium filling cavity 32 delivers a high current density out from port 313 in order to stimulate tissue when fixation member 34 is engaged within the tissue; the conductive medium filling cavity 32 may comprise a hydrogel, a saline solution, or blood as previously described.

In the foregoing specification, the invention has been described with reference to specific embodiments. However, it may be appreciated that various modifications and changes can be made without departing from the scope of the invention as set forth in the appended claims.

What is claimed is:

1. An implantable medical electrical lead, comprising:
   an elongated lead body having a proximal end and terminating at a distal end wall,
   a conductor extending from the proximal end of the elongated body toward the distal end wall,
      an electrode connected to the distal end wall of the elongated body, the electrode being adapted for stimulating myocardial tissue via intimate contact with the tissue
         the electrode being electrically coupled to the conductor,
         the electrode comprising a conductive structure having a first, interior surface defining a closed cavity within the electrode and having a second, exterior surface, wherein the first, interior surface of the conductive structure defines a first electrode surface;
      an insulative housing wrapping around the second, exterior surface of the conductive structure and having a port that circumscribes an area of the second, exterior surface of the conductive structure to define a second electrode surface;
      an ionically conductive fluid medium filling the cavity and being in intimate contact with the first electrode surface; and
      an insulated helical fixation member coupled to the insulative housing and extending distally therefrom;
   wherein, when a current is delivered, via the conductor, to the electrode, a first current density is generated at the first electrode surface and a second current density is generated at the second electrode surface, the first current density being smaller than the second current density; and
   when the helical fixation member is engaged in tissue, the second electrode surface forms a high impedance and low polarization tissue-stimulating electrode.

2. The lead of claim 1, wherein the second electrode surface protrudes from the port.

3. The lead of claim 2, wherein the second electrode surface is adapted to pierce tissue when the helical fixation member is engaged in tissue.

4. The lead of claim 1, wherein the second electrode surface is approximately flush with the port.

5. The lead of claim 1, wherein the conductive structure formed within the cavity comprises a proximal extension of the helical fixation member.

6. The lead of claim 1, wherein the conductive structure comprises a stud joining the helical fixation member to the conductor.

7. The lead of claim 1, wherein the port of the insulative housing has a cross-sectional area between approximately 0.1 square millimeters and 4.0 square millimeters.

8. The lead of claim 1, wherein the first electrode surface of the conductive structure is approximately greater than or equal to approximately 10 square millimeters.

9. The lead of claim 1, wherein the ionically conductive medium filling the cavity comprises a hydrogel.

10. The lead of claim 1, wherein the ionically conductive medium filling the cavity comprises a saline solution.

11. The lead of claim 1, wherein the electrode surface of the conductive structure comprises platinum black particles.

12. The lead of claim 1, wherein the conductive structure comprises an iridium-oxide.

13. The lead of claim 1, wherein the conductive structure comprises a ruthenium-oxide.

14. The lead of claim 1, wherein the conductive structure comprises titanium-nitride.

15. The lead of claim 1, further comprising a steroid-loaded MCRD formed about the insulative housing in proximity to the port.

16. The lead of claim 1, wherein the insulated helical fixation member comprises an oxide-coated tantalum.

17. The lead of claim 1 wherein the first electrode surface has a first surface area and the second electrode surface has a second surface area that is smaller than the first surface area.

* * * * *